United States Patent
Zhang et al.

(10) Patent No.: US 11,547,715 B2
(45) Date of Patent: Jan. 10, 2023

(54) USE OF CHLOROGENIC ACID IN PREPARATION OF DRUG FOR TREATING CHORDOMA

(71) Applicant: SICHUAN JIUZHANG BIOLOGICAL SCIENCE AND TECHNOLOGY CO., LTD, Sichuan (CN)

(72) Inventors: Jie Zhang, Sichuan (CN); Yazhuo Zhang, Sichuan (CN); Mengtian Zhang, Sichuan (CN)

(73) Assignee: SICHUAN JIUZHANG BIOLOGICAL SCIENCE AND TECHNOLOGY CO., LTD., Sichuan (CN)

( * ) Notice: Subject to any disclaimer, the term of this patent is extended or adjusted under 35 U.S.C. 154(b) by 0 days.

(21) Appl. No.: 16/958,881

(22) PCT Filed: Dec. 27, 2018

(86) PCT No.: PCT/CN2018/124310
§ 371 (c)(1),
(2) Date: Jun. 29, 2020

(87) PCT Pub. No.: WO2019/129135
PCT Pub. Date: Jul. 4, 2019

(65) Prior Publication Data
US 2020/0338104 A1    Oct. 29, 2020

(30) Foreign Application Priority Data

Dec. 28, 2017 (CN) .......................... 201711465147.8

(51) Int. Cl.
*A61K 31/7034*    (2006.01)
*A61P 35/00*       (2006.01)
*A61K 9/00*        (2006.01)
*A61K 9/19*        (2006.01)

(52) U.S. Cl.
CPC ........ *A61K 31/7034* (2013.01); *A61K 9/0019* (2013.01); *A61K 9/19* (2013.01); *A61P 35/00* (2018.01)

(58) Field of Classification Search
CPC .............. A61K 31/216; A61K 31/7034; A61K 9/0019; A61K 9/19; A61K 47/22; A61K 47/26; A61K 9/0095; A61K 9/2013; A61K 9/2018; A61K 9/2054; A61K 9/08; A61K 9/20; A61P 35/00
See application file for complete search history.

(56) References Cited

U.S. PATENT DOCUMENTS

2009/0076131 A1*  3/2009  Ricciardiello .......... A61P 35/00
                                              514/456

FOREIGN PATENT DOCUMENTS

CN        104758277    *    7/2015
CN        104758277 A       7/2015

OTHER PUBLICATIONS

Ji, Zhengang et al., "Expression and Clinical Implication of Hypoxia Inducible Factor-1 alpha and Multidrug Resistance Protein 1 in Chordoma", Medical Journal of Chinese People's Liberation Army, Jan. 1, 2010, pp. 42-44 *, Abstract.

* cited by examiner

*Primary Examiner* — Lezah Roberts
(74) *Attorney, Agent, or Firm* — Novick, Kim & Lee, PLLC; Allen Xue

(57) ABSTRACT

A drug that contains chlorogenic acid is effective in treating chordoma. When administered to a patient in need thereof, chlorogenic acid can significantly inhibit the proliferation of chordoma cells, reduce the expression level of multi-drug resistance gene MDR1 of chordoma cells, reverse the multi-drug resistance of chordoma cells, and effectively treat chordoma disease.

7 Claims, 1 Drawing Sheet

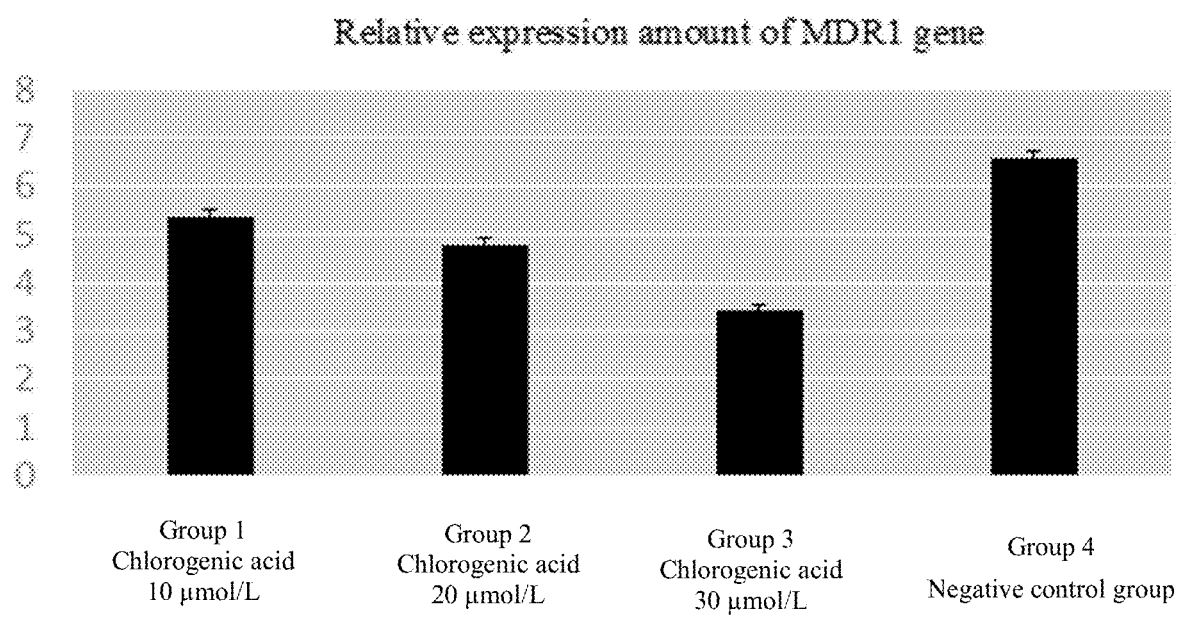

USE OF CHLOROGENIC ACID IN PREPARATION OF DRUG FOR TREATING CHORDOMA

TECHNICAL FIELD

The present invention relates to a new use of chlorogenic acid, and in particular to the use in the preparation of drugs for treatment of chordoma.

BACKGROUND ART

Chordoma is a rare malignant bone tumor originated from the residual chordate tissue in the embryonic period. The incidence of chordoma is about $4/1 \times 10^6$, and it is more common in the elderly. Its growth is relatively slow, and it is prone to sacrococcygeal region, skull base, cervical vertebrae, thoracolumbar vertebrae, and rarely outside the axial bone. Although chordoma is low to moderate malignant, 8%-43% of patients have advanced metastasis and poor prognosis. It is a relapse disease that is very difficult to cure.

Surgery is the main means for treatment of chordoma. Because of the extreme complexity of vertebrae anatomy, it is easy to cause incomplete tumor resection and higher local recurrence rate after operation, while extended resection will lead to related nerve injury and dysfunction, thus resulting in poor prognosis of chordoma, with a low feasibility. Postoperative radiotherapy is also an option for the treatment of the disease, but the effectiveness of this method has not been confirmed currently. Moreover, chemotherapeutic drugs have been considered to have no obvious therapeutic effect on chordoma, because chordoma cells have natural resistance to chemotherapeutic drugs.

According to the research, the failure in drug treatment of human chordoma is mainly due to the presence of MDR1 in human chordoma cells, whose expression rate is more than 10%. Its expression product P-glycoprotein (P-gp) will actively pump the drug out of the chordoma cells, that make the drug not enter the cells to exert its action, thus producing drug resistance. Therefore, it is the main focus of the research in this field to find suitable chemotherapeutic drugs and overcome the chemical resistance of chordoma.

At present, there is no literature report on the treatment of chordoma with chlorogenic acid.

CONTENT OF THE PRESENT INVENTION

The technical embodiments of the present invention provide a new use of chlorogenic acid. Overexpression of multidrug resistance gene 1 (MDR1) is the main cause of multidrug resistance in tumor cells. P-glycoprotein (P-gp), the expression product of MDR1, can transport drugs to outside of tumor cells and make cells form drug-resistance. By reducing the expression level of MDR1 gene, the chemotherapeutic effect can be effectively improved, and the clinical remission period be prolonged, thus playing a positive role in the treatment of chordoma.

Drug-resistant chordoma means developing drug resistance to antineoplastic agents, so that the antineoplastic effects of antineoplastic agents have obviously been declined, and even their effects are lost. Chordomas can be resistant per se or develop resistance to antineoplastic agents during treatment.

The present invention provides the use of chlorogenic acid in the preparation of drugs for treatment of chordoma.

Wherein, said chordoma is drug-resistant.

Wherein, said drug-resistant chordoma is the one caused by the expression of multidrug resistance gene MDR1 in chordoma cells.

Wherein, said drug is the one which can inhibit the proliferation of chordoma cells. Wherein, said drug is the one which can reduce the expression level of MDR1 gene in chordoma cells.

Wherein, said drug is prepared by taking chlorogenic acid as the active ingredient, with the addition of pharmaceutically acceptable excipients or auxiliary ingredients.

Wherein, said pharmaceutical preparation is an oral or injectable dosage form; preferably, said oral dosage form is a solution or a tablet; and said injectable dosage form is a freeze-dried powder injection.

Wherein, said preparation contains 1-225 mg chlorogenic acid/unit; the clinical dosage for said preparation is 1-450 mg/kg.

Wherein, when said preparation is an oral solution, each dosage unit contains 225 mg chlorogenic acid, and the clinical dosage is 225-450 mg/kg;

When said preparation is a tablet, each dosage unit contains 100 mg chlorogenic acid, and the clinical dosage is 100-200 mg/kg;

When said preparation is a freeze-dried powder injection, each dosage unit contains 30 mg chlorogenic acid, and the clinical dosage is 1-5 mg/kg.

The present invention further provides a method for treatment of chordoma, that includes chlorogenic acid is administrated to a patient.

Wherein, the clinical dosage of said chlorogenic acid is 225-450 mg/kg.

Wherein, when said preparation of chlorogenic acid is an oral solution, each dosage unit contains 225 mg chlorogenic acid, and the clinical dosage is 225-450 mg/kg; When said preparation of chlorogenic acid is a tablet, each dosage unit contains 100 mg chlorogenic acid, and the clinical dosage is 100-200 mg/kg; When said preparation of chlorogenic acid is a freeze-dried powder injection, each dosage unit contains 30 mg chlorogenic acid, and the clinical dosage is 1-5 mg/kg.

Wherein, said chordoma is drug-resistant.

Wherein, said drug-resistant chordoma is caused by MDR1 expressed by chordoma cells.

Wherein, said drug is the one which can inhibit the proliferation of chordoma cells.

Chlorogenic acid can significantly inhibit the proliferation of chordoma cells, reduce the expression level of MDR1 gene in chordoma cells, reverse the multidrug resistance of chordoma cells, effectively treat chordoma, and has a good clinical application prospect.

Obviously, based on above content of the present invention, according to the common technical knowledge and the conventional means in the field, without department from above basic technical spirits, other various modifications, alternations or changes can further be made.

By following specific examples, the present invention is further illustrated, but not limited. Based on above content of the present invention, according to the common technical knowledge and the conventional means in the field, without department from above basic technical spirits, other various modifications, alternations or changes can further be made.

DESCRIPTION OF FIGURES

FIG. 1 relative expression amount of MDR1 gene in human chordoma cells of different experimental groups.

EXAMPLES

Example 1 Preparation of Lyophilized Powder Injection with Chlorogenic Acid

1. Extraction of Chlorogenic Acid

The raw material of chlorogenic acid used in this example is extracted and purified from leaves of *Eucommia ulmoides*, with a purity of 99.6%.

2. Preparation of Lyophilized Powder Injection of Chlorogenic Acid 2.1 Formula

| | |
|---|---|
| Chlorogenic acid (principal agent) with a purity of 99.6% | 30 g |
| Mannitol (support agent) | 50 g |
| Vitamin C (antioxidant) | 10 g |

2.2 Preparative Method

Above formula was thoroughly dissolved in the water for injection. After filtration, 0.22 μm microfiltration membrane for removing bacteria was further used for fine filtration. After adjusting pH, 1000 of 2 ml powder injections were prepared according to the common procedure of sterile lyophilized powder. Each injection contained 30 mg chlorogenic acid, of which the content of chlorogenic acid was 33.3%.

Example 2 Preparation of Oral Solution with Chlorogenic Acid

1. Extraction of Chlorogenic Acid

Chlorogenic acid used in this example is extracted and purified from *Flos lonicerae*, with a purity of 98.47%.

2. Preparation of Oral Solution with Chlorogenic Acid 2.1 Formula

| | |
|---|---|
| Chlorogenic acid (principal agent) with a purity of 98.47% | 22.5 g |
| Vitamin C (antioxidant) | 15 g |
| Water for injection (solvent) | 10 L |

2.2 Preparative Method:

The amount of chlorogenic acid indicated in the formula and Vitamin C were taken out and dissolved in 10 L water for injection. According to the conventional preparative process of oral solution, after filtration, the solution was aseptically filled to obtain 100 bottles of oral solution, and each bottle contained 100 mL solution, i.e. 225 mg chlorogenic acid, of which the content of chlorogenic acid is 60%.

Example 3 Preparation of Tablets with Chlorogenic Acid

1. Extraction of Chlorogenic Acid

Chlorogenic acid used in this example is extracted and purified from *Flos lonicerae*, with a purity of 99.3%.

2. Preparation of Tablets with Chlorogenic Acid 2.1 Formula

| | |
|---|---|
| Chlorogenic acid (principal agent) with a purity of 99.3% | 100 g |
| Sugar powder (bulking agent) | 100 g |
| Lactose (bulking agent) | 200 g |
| Hydroxypropylmethylcellulose (binding agent) | 50 g |
| Magnesium stearate | 50 g |

2.2 Preparative Method:

In this example, chlorogenic acid tablet is prepared by wet granule pressing method. (1) The amount of hydroxypropylmethylcellulose as indicated in formula was taken out and dissolved in water to prepare water solution; (2) Chlorogenic acid, sugar powder and lactose were taken out as the amount shown in formula, mixed, and added to hydroxypropylmethylcellulose aqueous solution, then the mixture was well mixed to prepare soft material; (3) According to the conventional operation procedure of wet granulation, the resultant soft material was sieved, dried, and pelletized to get uniform size particles; (4) The resultant particles were mixed with magnesium stearate and pressed, thereby 1000 tablets were prepared, and each tablet contained 100 mg chlorogenic acid, in which the content of chlorogenic acid is 20%.

In the following, the beneficial effect of the present invention was proved by specific pharmacodynamic experiments:

Experimental Example 1 the Inhibition of Chlorogenic Acid on the Proliferation of Human Chordoma CM-319 Cells 1. Materials Drug: chlorogenic acid raw material (99.6% purity, Sichuan Jiuzhang Biotechnology Co., Ltd.) Cell line: human chordoma cell line CM-319 cells (West China Hospital, Sichuan University)

2. Experimental Method

Human chordoma CM-319 cells growing in logarithmic phase was collected, and the cell concentration was adjusted to $6 \times 10^5$ cells/ml with 1640 medium. 100 μL suspension of above cells was taken out and inoculated into 96 well plate, and each experimental group has three replicate wells. The detailed groups are shown in Table 1. To each well, was added 100 μL corresponding drugs, so that the final concentration of chlorogenic acid in the experimental group is 10 μmol/L, 20 μmol/L, and 40 μmol/L, respectively, and then the plate was further cultured for 24 hours. In the negative control group, no drug was added, and only the same volume of 100 μL culture medium was added. After 24 hours, 10 μL CCK-8 solution was added to each well, and the culture plate was incubated in the incubator for another one hour. The absorbance of each well was measured at 450 nm by ELISA. The inhibition of chlorogenic acid on human chordoma CM-319 cells was calculated at various concentrations by using the growth inhibition rate=(absorbance of the negative control group at 450 nm—absorbance of the experimental group at 450 nm)/absorbance of the negative control group at 450 nm×100%.

TABLE 1

Different experimental groups and chlorogenic acid concentrations.

| Experimental groups | Concentration of chlorogenic acid (μmol/L) |
|---|---|
| Group 1 | 10 |
| Group 2 | 20 |
| Group 3 | 40 |
| Group 4 (negative control group) | 0 |

3. Experimental Results

The proliferation of human chordoma CM-319 cells treated with different concentrations of chlorogenic acid was calculated, and the results are shown in Table 2:

TABLE 2

The inhibitory effect of chlorogenic acid at different concentrations
on the proliferation of human chordoma CM-319 cells

| Experimental groups | Inhibitory rate of cells (%) |
|---|---|
| Group 1 | 36.77 ± 5.12 |
| Group 2 | 48.37 ± 6.11 |
| Group 3 | 55.49 ± 3.78 |

In this example, CCK-8 test kit was used to detect the effect of chlorogenic acid on the proliferation of human chordoma CM-319 cells. The experimental results show that different concentrations of chlorogenic acid can strongly inhibit human chordoma cells and prevent the proliferation of cells, and this inhibition can improve as the increase of chlorogenic acid concentration, suggesting that chlorogenic acid can inhibit the growth of human chordoma cells, and this inhibition is dose-dependent to some extent.

Experimental Example 2. Effect of Chlorogenic Acid on MDR1 Expression in Human Chordoma Cells CM-319

1. Materials

MDR1 primer (Shanghai Bioengineering Co., Ltd.); RNA extraction kit (Jiangsu biyuntian); reverse transcription synthesis kit (Jiangsu biyuntian); chlorogenic acid API (purity 99.6%, Sichuan Jiuzhang Biotechnology Co., Ltd.).

2. Experimental Method

In this example, RT-PCR was used to detect the effect of different experimental groups on the expression of MDR1 in human chordoma CM-319 cells. The detailed experimental groups are shown in Table 3. CM-319 cells cultured in 6-well plate was collected, and RNA extraction kit was used to extract total RNA in cells, then reverse transcription synthesis kit was used to transcribe the first strand of cDNA. After that, PCR amplification reaction was used to detect the expression level of target genes in different experimental groups.

TABLE 3

Different experimental groups and chlorogenic acid concentrations.

| Experimental groups | Concentration of chlorogenic acid (μmol/L) |
|---|---|
| Group 1 | 10 |
| Group 2 | 20 |
| Group 3 | 40 |
| Group 4 (Negative control group) | 0 |

3. Experimental Results

The results of RT-PCR showed that different concentrations of chlorogenic acid could reduce the expression level of MDR1 in CM-319 cells to various degrees, in which high concentration of chlorogenic acid (40 μmol/L) could significantly reduce the expression level of drug-resistant genes in cells compared with other groups, and further improve the sensitivity of tumor cells to drugs. The test results are shown in FIG. 1.

In summary, chlorogenic acid can significantly inhibit the proliferation of chordoma cells, reduce the expression level of MDR1 gene in chordoma cells, reverse the multidrug resistance of chordoma cells, effectively treat chordoma, and has a good clinical application prospect.

The invention claimed is:

1. A method for treatment of chordoma, comprising administering an effective amount of a composition to a patient in need thereof, wherein the composition comprises chlorogenic acid at a dosage of 30-40 μmol/L.

2. The method according to claim 1, wherein preparation of said chlorogenic acid is an oral solution.

3. The method according to claim 1, wherein said chordoma is drug-resistant.

4. The method according to claim 3, wherein said drug-resistant chordoma is caused by MDR1 expressed by chordoma cells.

5. The method according to claim 4, wherein said chlorogenic acid is the one which can inhibit the proliferation of chordoma cells.

6. The method according to claim 2, wherein said preparation is a tablet.

7. The method according to claim 2, wherein said preparation is a freeze-dried powder injection.

* * * * *